US011154528B2

(12) United States Patent
Poulsen et al.

(10) Patent No.: US 11,154,528 B2
(45) Date of Patent: *Oct. 26, 2021

(54) EXTENDED DURATION LOCAL ANESTHETIC FORMULATION

(71) Applicant: Ventis Pharma, Dakota Dunes, SD (US)

(72) Inventors: Jeremy Poulsen, N Sioux City, SD (US); Louis Stanfield, Odessa, FL (US); Lawrence Volz, Dakota Dunes, SD (US)

(73) Assignee: Ventis Pharma, Dakota Dunes, SD (US)

( * ) Notice: Subject to any disclaimer, the term of this patent is extended or adjusted under 35 U.S.C. 154(b) by 124 days.

This patent is subject to a terminal disclaimer.

(21) Appl. No.: 16/148,080

(22) Filed: Oct. 1, 2018

(65) Prior Publication Data

US 2019/0029988 A1 Jan. 31, 2019

Related U.S. Application Data

(62) Division of application No. 14/960,214, filed on Dec. 4, 2015, now Pat. No. 10,117,847.

(51) Int. Cl.
| | | |
|---|---|---|
| *A61K 31/565* | (2006.01) | |
| *A61K 31/16* | (2006.01) | |
| *A61K 31/137* | (2006.01) | |
| *A61K 31/245* | (2006.01) | |
| *A61J 1/20* | (2006.01) | |
| *A61K 31/573* | (2006.01) | |
| *A61K 45/06* | (2006.01) | |
| *A61K 47/02* | (2006.01) | |
| *B65D 81/32* | (2006.01) | |
| *A61K 9/08* | (2006.01) | |
| *A61K 9/00* | (2006.01) | |

(52) U.S. Cl.
CPC ........... *A61K 31/245* (2013.01); *A61J 1/2093* (2013.01); *A61K 31/137* (2013.01); *A61K 31/573* (2013.01); *A61K 45/06* (2013.01); *A61K 47/02* (2013.01); *B65D 81/3266* (2013.01); *A61K 9/0019* (2013.01); *A61K 9/08* (2013.01)

(58) Field of Classification Search
CPC ..... A61K 31/565; A61K 31/16; A61K 31/137
USPC ........................................ 514/171, 626, 649
See application file for complete search history.

(56) References Cited

U.S. PATENT DOCUMENTS

| | | |
|---|---|---|
| 5,942,543 A | 8/1999 | Ernst |
| 5,954,703 A | 9/1999 | Golub |
| 6,708,822 B1 | 3/2004 | Muni |
| 9,186,299 B1 | 11/2015 | Levi et al. |
| 10,117,847 B2 * | 11/2018 | Poulsen ................. A61K 45/06 |
| 2001/0055607 A1 | 12/2001 | Levin |
| 2004/0142968 A1 | 7/2004 | Price et al. |
| 2014/0329841 A1 | 11/2014 | Berde et al. |
| 2015/0010528 A1 | 1/2015 | Weg |

FOREIGN PATENT DOCUMENTS

| | | |
|---|---|---|
| CN | 1197636 A | 11/1998 |
| CN | 1069826 C | 8/2001 |
| JP | H10-5309 A | 1/1998 |
| JP | 2006513224 A | 4/2006 |
| JP | 2012143629 A | 8/2012 |
| JP | 2014519938 A | 8/2014 |
| WO | 9202271 A1 | 2/1992 |
| WO | 9634599 A1 | 11/1996 |
| WO | 2004058329 A2 | 7/2004 |
| WO | 2006076663 A2 | 7/2006 |
| WO | 2012175753 A1 | 12/2012 |
| WO | 2014171986 A1 | 10/2014 |
| WO | 2015126942 A1 | 8/2015 |

OTHER PUBLICATIONS

Dull et al., "Variations in the Composition of Spinal Anesthetic Solutions: The effects of Drug Addition Order and Preparation Methods" Anesth. Analg. 1998, 87, 1326-30.*
Singer et al., Academic Emergency Medicine, (Mar. 2001), 8(3), 223-230.*
Kamiya et al., "Lidocaine Concentration in Cerebrospinal Fluid after Epidural Administration" Anesthesiology, 2009, 110, 1127-32.*
Young et al., "Clinical Implications of the Transversus Abdominis Plane Block in Adults," Anesthesiology Research and Practice, vol. 2012, pp. 1-11 (2011).
MacMahon et al., "Injectable Corticosteriod and Local Anesthetic Preparations: A Review for Radiologists," Radiology, vol. 252, No. 3, pp. 647-661 (Sep. 2009).
Kuta et al., "pH Adjustment Schedule for the Amide Local Anesthetics," Regional Anesthesia, vol. 14, No. 5, pp. 229-235 (Sep./Oct. 1989) (Abstract).
Yagiela et al., "Comparison of Myotoxic Effects of lidocaine with Epinephrine in Rats and Humans" Anesth Analg, 60, pp. 471-480, 1981.
Excerpt from Micromedex Red Book found at <http://truvenhealth.com/Products/Micromedex/Product-Suites/Clinical-Knowledge/Red-Book> (accessed on Aug. 7, 2018).
Giordano et al., "Topical local anesthesia: focus on lidocaine-tetracaine combination," Local and Regional Anesthesia, vol. 8, pp. 95-100 (2015).

(Continued)

*Primary Examiner* — Raymond J Henley, III
(74) *Attorney, Agent, or Firm* — Ice Miller LLP

(57) ABSTRACT

An extended duration anesthetic includes a short duration local anesthetic in a dilute solution and a long duration local anesthetic. The long duration local anesthetic is maintained in a powdered form until the time of administration. Premeasured quantities of the dilute solution and powdered long duration local anesthetic in a kit allow for quick preparation of a solution with desired concentrations of both short duration local anesthetic and long duration local anesthetic at the time of administration.

20 Claims, 16 Drawing Sheets

(56) References Cited

OTHER PUBLICATIONS

Hartman et al., "Duplex drug-delivery pouch," 31 Aug. 2003, XP-002786230, Retrieved from the Internet: URL: https://www.packagingdigest.com/pouches/duplex-drug-delivery-pouch, pp. 1-11.
Liu et al., "Epinephrine Prolongs Duration of Subcutaneous Infiltration of Local Anesthesia in a Dose-related Manner," Regional Anesthesia, vol. 20, No. 5, pp. 378-384 (1995).
Yamamoto et al., "Efficacy of Repeated Subcostal Transversus Abdominis Plane Blocks with 0.2% Lidocaine via 18-gauge Intravenous Catheters in Patients Undergoing Abdominal Aortic Aneurism Surgery," Masui (Anesthesia), vol. 63, No. 8, pp. 866-871 (2014) (Last Page English Abstract).

* cited by examiner

TETRACAINE

AMBUCAINE

AMYLOCAINE

ARTICAINE

BENZOCAINE

BENZONATATE

BUPIVACAINE

BUTACAINE

BUTANILICAINE

CHLOROPROCAINE

CINCHOCAINE

COCAINE

CYCLOMETHYCAINE

DIPERODON

DIMETHISOQUIN

DIMETHOCAINE

ETIDOCAINE

HEXYLCAINE

HYDROXYPROCAINE

ISOBUCAINE

LEVOBUPIVACAINE

LIDAMIDINE

LIDOCAINE

MEPIVACAINE

MEPRYLCAINE

METABUTOXYCAINE

ORTHOCAINE

OXETACAINE

OXYBUPROCAINE

PARAETHOXYCAINE

PHENACAINE

PIPEROCAINE

PIRIDOCAINE

PRAMOCAINE

PRILOCAINE

PROCAINAMIDE

PROCAINE

PROPOXYCAINE

PYRROCAINE

QUINISOCAINE

ROPIVICAINE

TOLYCAINE

TRIMECAINE

TROPACOCAINE

EPINEPHRINE

EXTENDED DURATION LOCAL ANESTHETIC FORMULATION

CROSS REFERENCE TO RELATED APPLICATIONS

This application is a divisional application of U.S. patent application Ser. No. 14/960,214, filed Dec. 4, 2015, now U.S. Patent No. 10,117,847 the disclosure of which is incorporated herein by reference in its entirety.

FIELD OF THE INVENTION

Embodiments of the inventive concepts disclosed herein are directed generally toward local anesthetics, and more particularly toward long duration local anesthetics for producing extended analgesia during surgical procedures.

BACKGROUND

Local anesthesia describes any technique to induce the absence of sensation in a specific part of the body, generally with the aim of inducing local analgesia or local insensitivity to pain. Regional anesthesia is aimed at anesthetizing a larger part of the body such as an arm, leg or region of the trunk, usually by blocking the function of a specific nerve or nerves. Generally, various local anesthetics are injected into the surgical site or into sites adjacent to specific nerves to provide analgesia to a specific region. Medications currently in use will generally provide analgesia for between two and eighteen hours. A proprietary formulation of bupivacaine liposomal, marketed under the trademark Exparel, has a stated duration up to 72 hours, but such duration is generally not actually seen. Furthermore, certain features of Exparel and other similar products are highly toxic, limiting the doses employed.

Local and regional anesthesia, as compared to general anesthesia, allows patients to undergo surgical procedures with less pain and stress, and decreases the need for narcotics during and after surgery leading to improved post-surgical recovery. There has long been a need by physicians to provide local or regional anesthesia for an extended period of time (thirty-six to forty-eight hours or longer) to provide significant postoperative pain relief until the pain from the surgical procedure has resolved sufficiently to be controlled with oral narcotics or without opioid analgesics at all. Furthermore, sufficient treatments for chronic pain due to tissue pathologies and neuropathic pain due to peripheral nerve or central nervous system damage are needed.

Pain relief research during the last two decades has focused on the identification of new local anesthetic formulations to produce analgesia of long duration with minimal impairment of autonomic function and low toxicity. For analgesia purposes, minimal or no motor blockade is desirable. Bupivacaine and etidocaine reportedly offer major nerve block for three to twelve hours; unfortunately, each of these local anesthetics also is highly cardiotoxic and deaths are possible from vascular absorption. Some existing products utilize high concentrations (approximately 2%) of bupivacaine, which has also resulted in deaths.

Consequently, it would be advantageous if a drug or combination of drugs existed that is suitable for providing extended duration local or regional analgesia for surgical procedures and which exhibits minimal toxicity.

SUMMARY

Accordingly, embodiments of the inventive concepts disclosed herein are directed to a novel method and apparatus for providing extended duration local or regional analgesia for surgical procedures.

In one aspect, embodiments of the inventive concepts disclosed herein are directed to a kit for providing extended duration local or regional analgesia during a surgical procedure. The kit includes a local, short term anesthetic in solution and a powdered preparation of tetracaine. The solution and powdered preparation are maintained in separate chambers of a multi-chamber storage device; the separate chambers separated by a breachable barrier. Squeezing the solution chamber breaches the barrier, mixing the solution and the powdered preparation in a predetermined ratio. The kit provides either blunt needle access or a needleless access port to withdraw the mixture. The mixture is then injected locally or regionally as necessary.

It is to be understood that both the foregoing general description and the following detailed description are exemplary and explanatory only and should not restrict the scope of the claims. The accompanying drawings, which are incorporated in and constitute a part of the specification, illustrate exemplary embodiments of the inventive concepts disclosed herein and together with the general description, serve to explain the principles.

BRIEF DESCRIPTION OF THE DRAWINGS

The numerous advantages of the embodiments of the inventive concepts disclosed herein may be better understood by those skilled in the art by reference to the accompanying figures in which:

FIG. 2-1 shows a chemical structure of ambucaine;
FIG. 2-2 shows a chemical structure of amylocaine;
FIG. 2-3 shows a chemical structure of articaine;
FIG. 2-4 shows a chemical structure of benzocaine;
FIG. 2-5 shows a chemical structure of benzonatate;
FIG. 2-6 shows a chemical structure of bupivacaine;
FIG. 2-7 shows a chemical structure of butacaine;
FIG. 2-8 shows a chemical structure of butanilicaine;
FIG. 2-9 shows a chemical structure of chloroprocaine;
FIG. 2-10 shows a chemical structure of cinchocaine;
FIG. 2-11 shows a chemical structure of cocaine;
FIG. 2-12 shows a chemical structure of cyclomethycaine;
FIG. 2-13 shows a chemical structure of diperodon;
FIG. 2-14 shows a chemical structure of dimethisoquin;
FIG. 2-15 shows a chemical structure of dimethocaine;
FIG. 2-16 shows a chemical structure of etidocaine;
FIG. 2-17 shows a chemical structure of hexylcaine;
FIG. 2-18 shows a chemical structure of hydroxyprocaine;
FIG. 2-19 shows a chemical structure of isobucaine;
FIG. 2-20 shows a chemical structure of levobupivacaine;
FIG. 2-21 shows a chemical structure of lidamidine;
FIG. 2-22 shows a chemical structure of lidocaine;
FIG. 2-23 shows a chemical structure of mepivacaine;
FIG. 2-24 shows a chemical structure of meprylcaine;
FIG. 2-25 shows a chemical structure of metabutoxycaine;
FIG. 2-26 shows a chemical structure of orthocaine;
FIG. 2-27 shows a chemical structure of oxetacaine;
FIG. 2-28 shows a chemical structure of oxybuprocaine;
FIG. 2-29 shows a chemical structure of paraethoxycaine;

FIG. 2-30 shows a chemical structure of phenacaine;
FIG. 2-31 shows a chemical structure of piperocaine;
FIG. 2-32 shows a chemical structure of piridocaine;
FIG. 2-33 shows a chemical structure of pramocaine;
FIG. 2-34 shows a chemical structure of prilocaine;
FIG. 2-35 shows a chemical structure of procainamide;
FIG. 2-36 shows a chemical structure of procaine;
FIG. 2-37 shows a chemical structure of propoxycaine;
FIG. 2-38 shows a chemical structure of pyrrocaine;
FIG. 2-39 shows a chemical structure of quinisocaine;
FIG. 2-40 shows a chemical structure of ropivicaine;
FIG. 2-41 shows a chemical structure of tolycaine;
FIG. 2-42 shows a chemical structure of timecaine;
FIG. 2-43 shows a chemical structure of tropacocaine;
FIG. 3 shows a chemical structure of epinephrine;
FIG. 4 shows one embodiment of a storage package according to the inventive concepts disclosed herein;
FIG. 5 shows a cross-sectional view of the package shown in FIG. 4;
FIG. 6 shows an environmental view of one embodiment of a kit according to the inventive concepts disclosed herein during mixing;
FIG. 7 shows a cross-sectional view of the package shown in FIGS. 4 and 5 during mixing;
FIG. 8 shows a cross-sectional, environmental view of the package shown in FIG. 7 with contents mixed;
FIG. 9 shows an environmental view of one embodiment according to the inventive concepts disclosed herein;

DETAILED DESCRIPTION

Reference will now be made in detail to the subject matter disclosed, which is illustrated in the accompanying drawings. The scope of the inventive concepts disclosed herein is limited only by the claims; numerous alternatives, modifications and equivalents are encompassed. For the purpose of clarity, technical material that is known in the technical fields related to the embodiments has not been described in detail to avoid unnecessarily obscuring the description.

In one aspect of the inventive concepts disclosed herein, a mixture of tetracaine and a short duration local anesthetic selected from a class of such anesthetics provides local or regional analgesia beginning less than five minutes after injection, and lasting more than twenty-four hours. In another aspect, the mixture is produced at the time of application from a solution including the short duration local anesthetic and a powdered preparation of tetracaine. The powdered preparation of tetracaine allows for an anesthetic formulation that does not require refrigeration. Embodiments of the present invention are particularly useful for treating localized pain that is attributable to a nociceptor-mediated pain resulting from surgery or injury.

Figure 1:
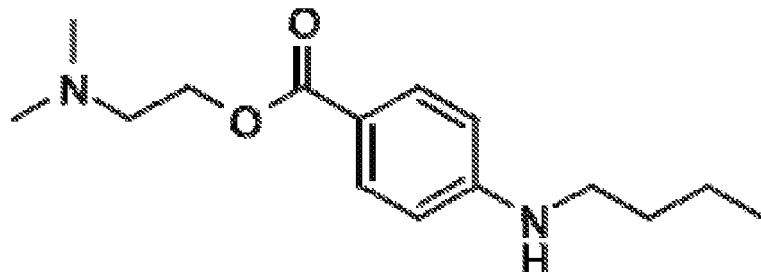
FIG. 1 shows a chemical structure of tetracaine.

Referring to FIG. 1, a chemical structure of tetracaine is shown. Tetracaine is a long duration local anesthetic. Alternative long duration local anesthetics carry significant risks; including seizures, cardiac arrest, and death should intravascular injection occur. Tetracaine is immediately metabolized in contact with blood, ameliorating risks associated with unintentional intravascular injection and therefore carries minimal risk.

Tetracaine is currently available in solution for use as a topical or spinal anesthetic but requires refrigeration once in solution. Refrigeration makes tetracaine solutions difficult to store in pharmacies, more expensive to stock, and places the solution at risk for degradation if not administered before the solution returns to room temperature. In powdered form, tetracaine is stable at room temperature.

Referring to FIGS. 2-1 through 2-43, chemical structures of short duration local anesthetics ambucaine; amylocaine; articaine; benzocaine; benzonatate; bupivacaine; butacaine; butanilicaine; chloroprocaine; cinchocaine; cocaine; cyclomethycaine; diperodon; dimethisoquin; dimethocaine; etidocaine; hexylcaine; hydroxyprocaine; isobucaine; levobupivacaine; lidamidine; lidocaine; mepivacaine; meprylcaine; metabutoxycaine; orthocaine; oxetacaine; oxybuprocaine; paraethoxycaine; phenacaine; piperocaine; piridocaine; pramocaine; prilocaine; procainamide; procaine; propoxycaine; pyrrocaine; quinisocaine; ropivicaine; tolycaine; timecaine; and tropacocaine respectively are shown. Short duration local anesthetics are generally used in 1%-2% concentrations. Current applications for short duration local anesthetics are dictated by toxicity; these toxicities vary by drug. For the most commonly used short acting local anesthetic drug, lidocaine, a dose of 3 mg per kilogram, without epinephrine, or 7 mg/kg with epinephrine, is toxic in the event of intravascular absorption. Intravascular injection or a toxic dosage carries the risk of potential complications such as cardiac arrhythmias or seizures. For the most commonly used longer acting local anesthetic, bupivacaine, the toxic dose with or without epinephrine is 2.5 mg per kg. This dose can lead to cardiac rhythm disturbances including long duration blockade of the cardiac conduction system, producing death in most instances in which this occurs.

Because of the inherent and serious toxicity issues with bupivacaine, techniques of local and regional anesthesia relying predominantly on bupivacaine minimize the total dose of anesthetic employed in any situation to minimize the severe consequences of overdose. A hypothetical 70 kg patient can only receive a maximum of 70 ml of 0.25% bupivacaine. For the more concentrated and longer acting 0.5% bupivacaine, the total dose would be 35 ml. The recommended volume of bupivacaine based anesthetic for a transversus abdominis plane (TAP) block is therefore 30-35 ml per side. This block is commonly used in patients undergoing abdominal procedures, resulting in an analgesic duration of 12-16 hours. Using embodiments of the present invention, the same TAP block can be performed with 50 ml per side, leading to a longer duration (in addition to the longer duration afforded by the intrinsic effect of the formulation).

The same is true with other types of regional anesthetics. Axillary and interscalene blocks are typically performed with 30 ml or less of bupivacaine based anesthetic. Up to 50 ml of anesthetic according to embodiments of the present invention is safe and provides both the intrinsically longer duration and the longer duration afforded by the larger volume deposited in the neurovascular sheath. A 0.2% concentration of tetracaine is not neurotoxic and produces minimal motor blockade, allowing longer and more complete sensory blockade, which is ideal for postoperative analgesia. The dose is body habitus dependent, not age dependent, and is therefore safe in the pediatric population. Generally, younger patients, who are faster metabolizers, tend to have somewhat shorter durations of effect than older patients.

Unlike extended release formulations of bupivacaine based products, which retain the undesirable toxicity of the parent compound, embodiments of the present invention are safe and effective across the spectrum of patients. Because tetracaine is an ester whose degradation product is para-aminobenzoic acid, there is a very small fraction of the population who may exhibit sensitivity to PABA. However, another PABA congener, methylparaben, is a commonly used preservative for many OTC drugs and sunscreens, so the numbers of people likely to be adversely affected by tetracaine is extremely small. Even frank anaphylaxis to PABA is easily treatable with epinephrine, unlike the costly, laborious, and highly problematic issues associated with treatment of bupivacaine toxicity.

In one embodiment, a dilute solution of short duration local anesthetic virtually eliminates the risk associated with intravascular injection. A dilute solution may comprise no more than 0.5% of short duration local anesthetic. A dilute solution does not impact efficacy as the concentration allows for quick onset of effect but the primary analgesia is a result of a long duration local anesthetic component.

Figures 1, 2:
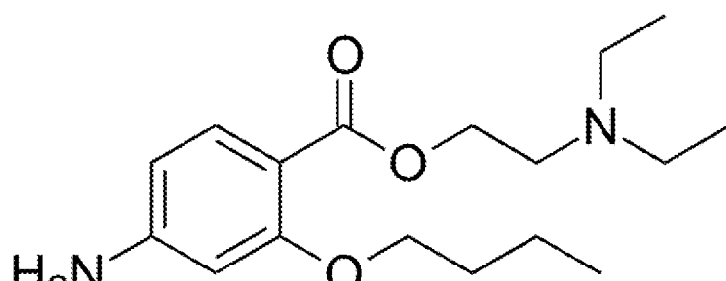
Figure 2:
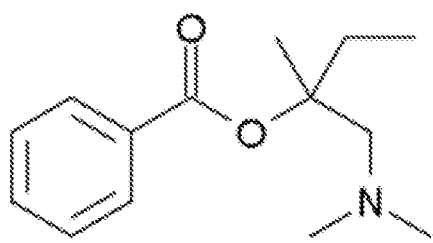
Figures 2, 3:
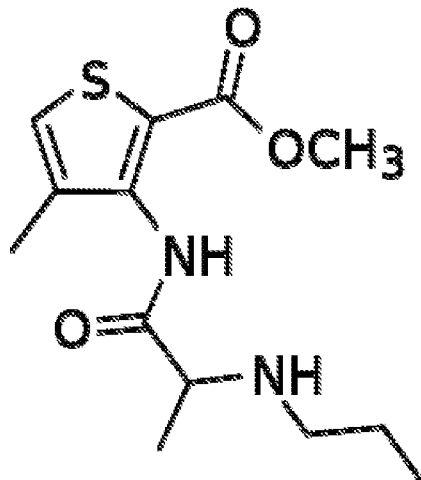

Referring to FIG. 3, a chemical structure of epinephrine is shown. In one embodiment, where a dilute solution of short duration local anesthetic such as shown in FIGS. 2-1 through 2-43 is used, the solution may further include epinephrine to minimize or eliminate the risk of potential overdose, minimize or eliminate the risks due to toxicity of the short duration local anesthetic, and extend the duration of analgesia. A dilute solution having 0.5% of a short duration local anesthetic and between one part per 250,000 and one part per 50,000 epinephrine virtually ensures the amount of short duration local anesthetic would not reach toxic levels.

Figures 2, 3, 4:
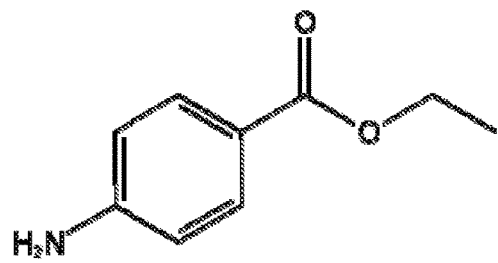

Referring to FIG. 4, one embodiment of a storage package 400 according to the inventive concepts disclosed herein is shown. The package 400 comprises a solution compartment 402 and a powder compartment 404 separated by a breachable barrier 406. The solution compartment 402 may be configured to contain a solution of short duration local anesthetic. The powder compartment 404 may be configured to contain a powdered preparation of long duration anesthetic. The breachable barrier 406 may be configured to maintain separation of the contents of the solution compartment 402 and the powder compartment 404 during normal handling. When sufficient external pressure is applied to the solution compartment 402, the breachable barrier 406 is breached and the contents of the solution compartment 402 may mix with and dissolve the contents of the powder compartment 404. The mixed contents may then be withdrawn, via a syringe, through an outlet port 408. A person skilled in the art may appreciate that the package 400 shown is exemplary only, and that other packaging options may be employed. Any packaging option that separates a solution and a powder component, and allows such components to be mixed just prior to the time of administration may be employed.

Figures 2, 3, 4, 5:
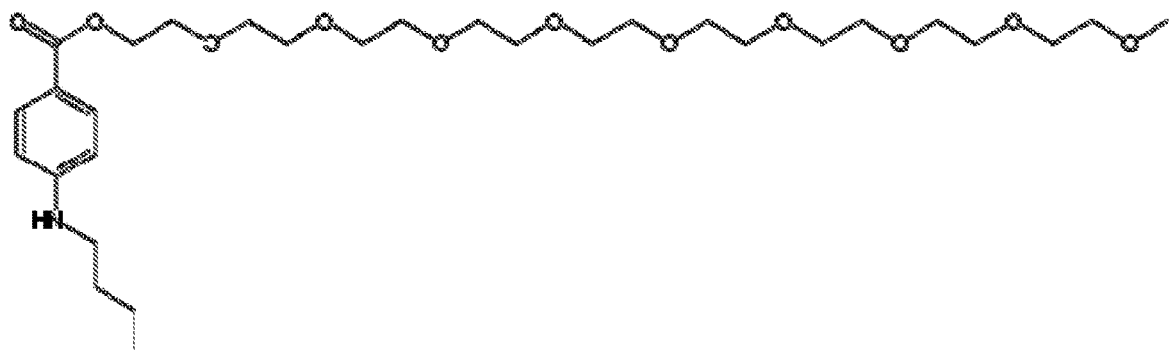

Referring to FIG. 5, a cross-sectional view of the package 400 shown in FIG. 4 is shown. In one embodiment, the solution compartment 402 contains a solution 502 comprising at least one short duration local anesthetic such as shown in FIGS. 2-1 through 2-43. The solution 502 may be a dilute solution 502 comprising no more than 0.5% short duration local anesthetic. The solution 502 may further comprise epinephrine to enhance the efficacy of the short duration local anesthetic and to reduce toxicity.

The powder compartment 404 contains a powdered tetracaine composition 504. The quantity of powdered tetracaine composition 504 is related to the quantity of solution 502 such that when mixed, a desirable concentration of tetracaine is dissolved into the solution 502.

Figures 2, 3, 4, 5, 6:
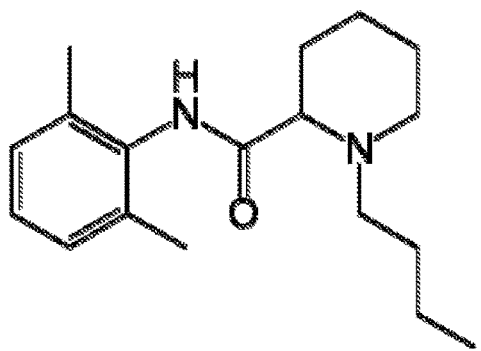

Referring to FIG. 6, an environmental view of one embodiment such as shown in FIG. 4 during mixing is shown. With sufficient pressure applied to the solution compartment of the package 404, the breachable barrier 406 is ruptured and the solution compartment and powder compartment are joined to allow mixing of the contained solution and powdered tetracaine composition.

A package 400 according to embodiments of the present invention may be stored at room temperature without risking degradation of the powdered tetracaine composition. Because the package 400 includes premeasured quantities of short duration local anesthetic solution and long duration local anesthetic in the form of the tetracaine powder composition, final mixing can be easily performed at the time of use.

Figures 2, 3, 4, 5, 6, 7:
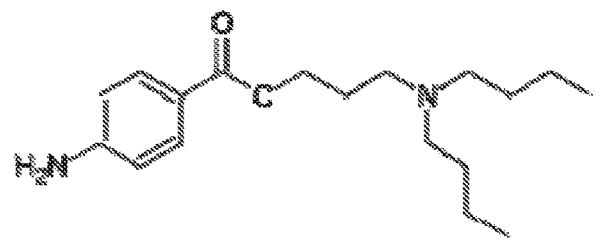
Figures 2, 3, 4, 5, 6, 7, 8:
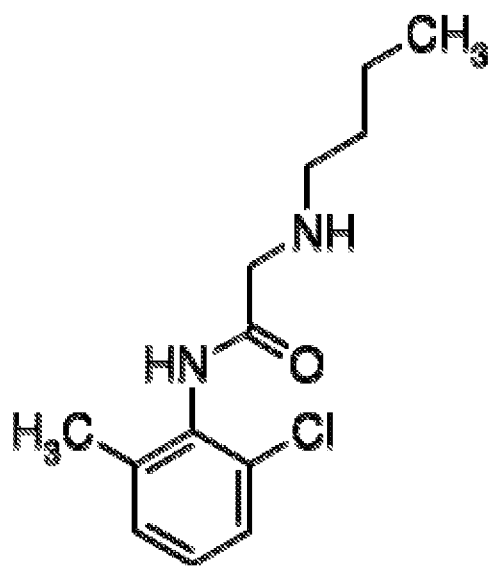
Figures 2, 3, 4, 5, 6, 7, 8, 9:
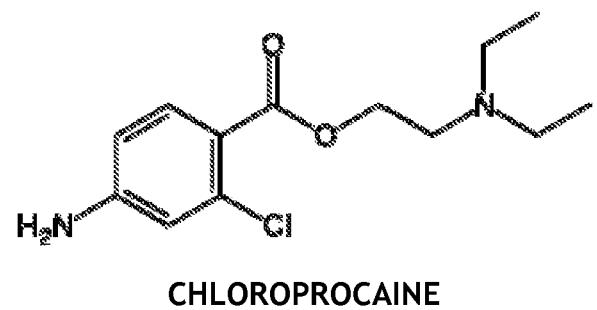
Figures 2, 3, 4, 5, 6, 7, 8, 9, 10:
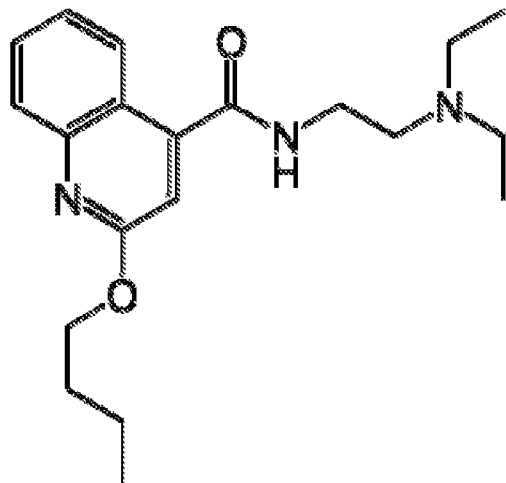
Figures 2, 3, 4, 5, 6, 7, 8, 9, 10, 11:
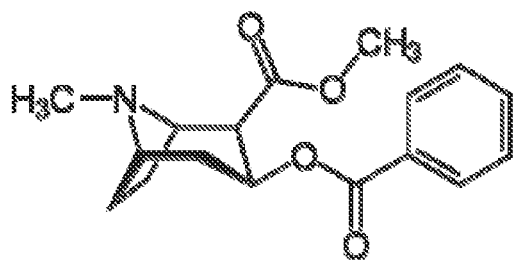
Figures 2, 3, 4, 5, 6, 7, 8, 9, 10, 11, 12:
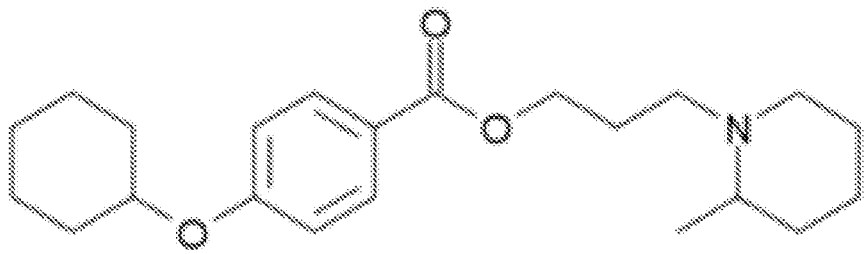
Figures 2, 3, 4, 5, 6, 7, 8, 9, 10, 11, 12, 13:
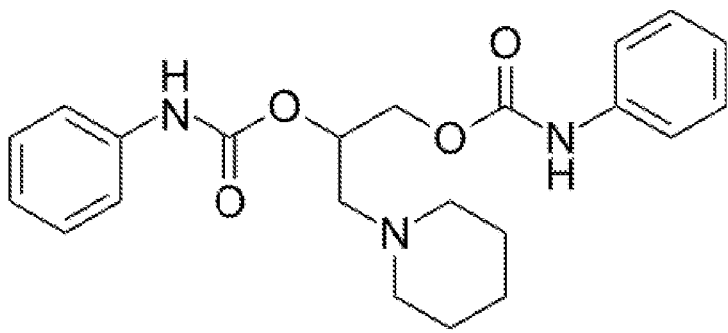
Figures 2, 3, 4, 5, 6, 7, 8, 9, 10, 11, 12, 13, 14:
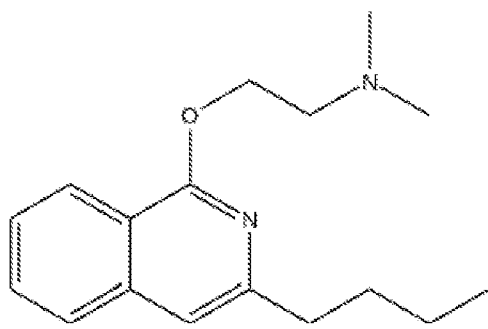
Figures 2, 3, 4, 5, 6, 7, 8, 9, 10, 11, 12, 13, 14, 15:
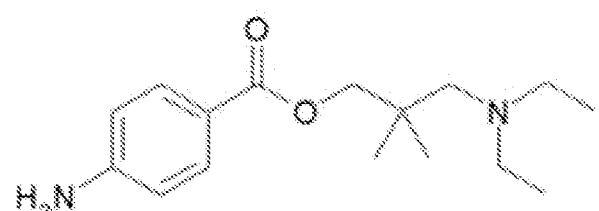
Figures 2, 3, 4, 5, 6, 7, 8, 9, 10, 11, 12, 13, 14, 15, 16:
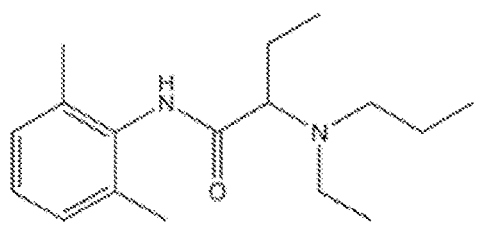
Figures 2, 3, 4, 5, 6, 7, 8, 9, 10, 11, 12, 13, 14, 15, 16, 17:
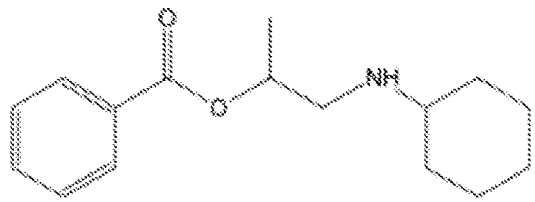
Figures 2, 3, 4, 5, 6, 7, 8, 9, 10, 11, 12, 13, 14, 15, 16, 17, 18:
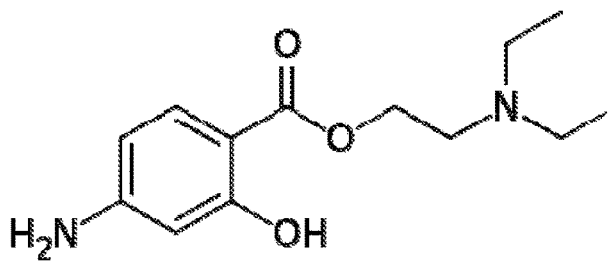
Figures 2, 3, 4, 5, 6, 7, 8, 9, 10, 11, 12, 13, 14, 15, 16, 17, 18, 19:
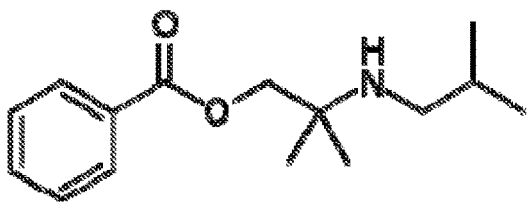
Figures 2, 3, 4, 5, 6, 7, 8, 9, 10, 11, 12, 13, 14, 15, 16, 17, 18, 19, 20:
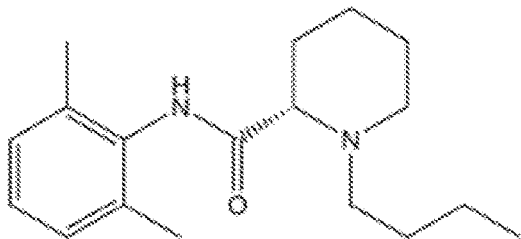
Figures 2, 3, 4, 5, 6, 7, 8, 9, 10, 11, 12, 13, 14, 15, 16, 17, 18, 19, 20, 21:
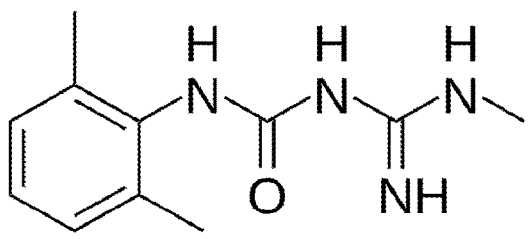
Figures 2, 3, 4, 5, 6, 7, 8, 9, 10, 11, 12, 13, 14, 15, 16, 17, 18, 19, 20, 21, 22:
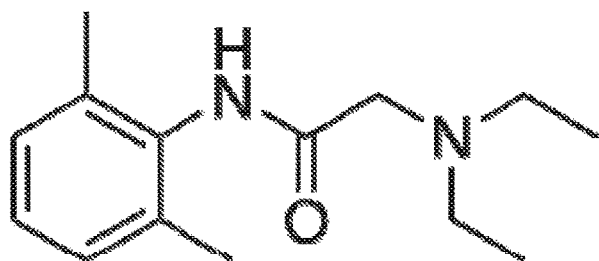
Figures 2, 3, 4, 5, 6, 7, 8, 9, 10, 11, 12, 13, 14, 15, 16, 17, 18, 19, 20, 21, 22, 23:
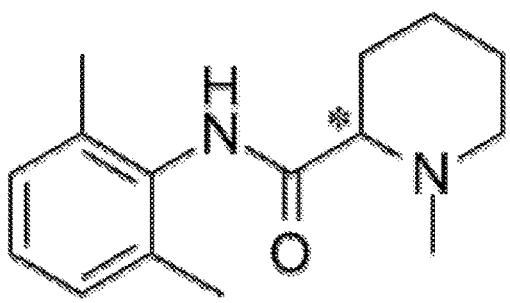
Figures 2, 3, 4, 5, 6, 7, 8, 9, 10, 11, 12, 13, 14, 15, 16, 17, 18, 19, 20, 21, 22, 23, 24:
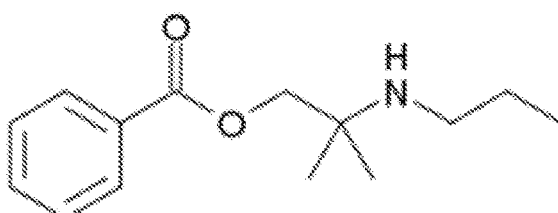
Figures 2, 3, 4, 5, 6, 7, 8, 9, 10, 11, 12, 13, 14, 15, 16, 17, 18, 19, 20, 21, 22, 23, 24, 25:
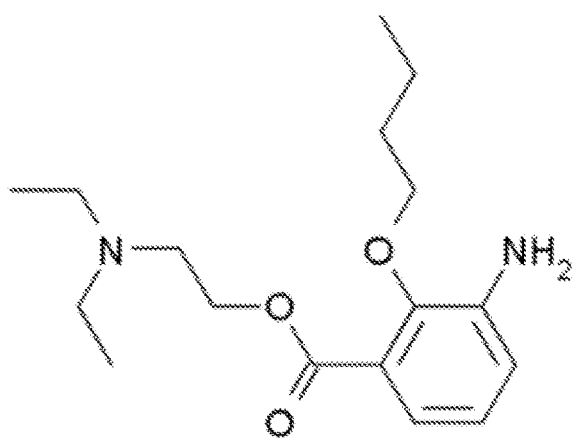
Figures 2, 3, 4, 5, 6, 7, 8, 9, 10, 11, 12, 13, 14, 15, 16, 17, 18, 19, 20, 21, 22, 23, 24, 25, 26:
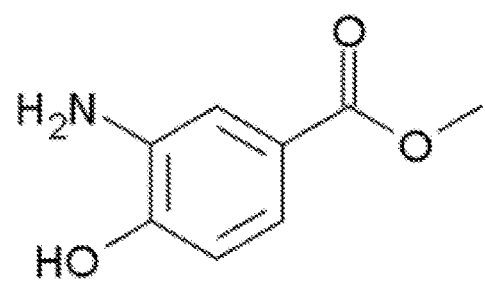
Figures 2, 3, 4, 5, 6, 7, 8, 9, 10, 11, 12, 13, 14, 15, 16, 17, 18, 19, 20, 21, 22, 23, 24, 25, 26, 27:
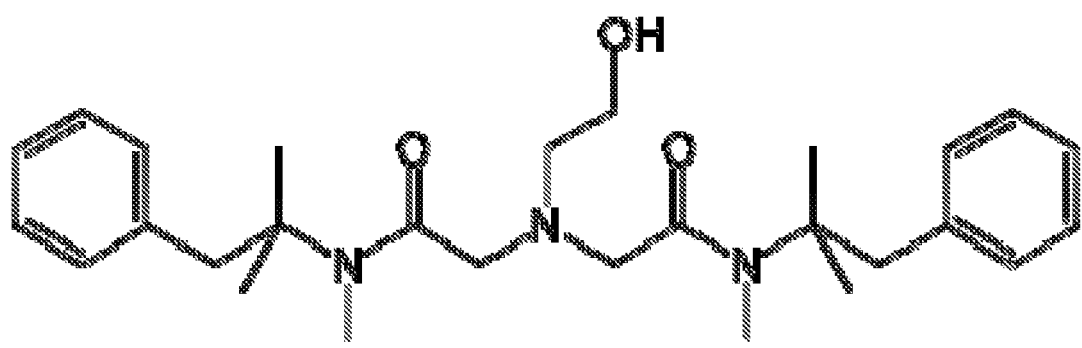
Figures 2, 3, 4, 5, 6, 7, 8, 9, 10, 11, 12, 13, 14, 15, 16, 17, 18, 19, 20, 21, 22, 23, 24, 25, 26, 27, 28:
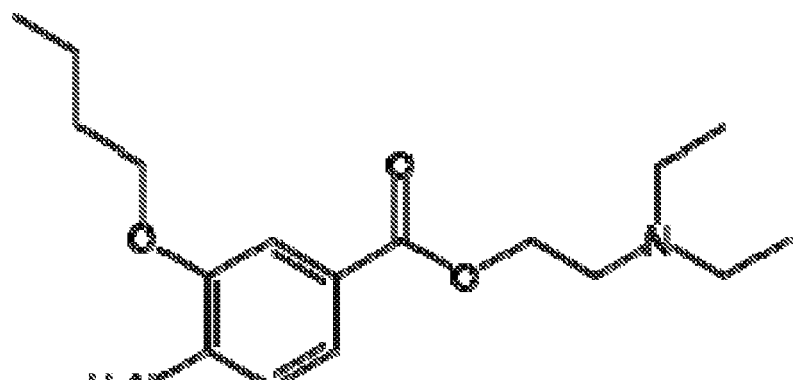
Figures 2, 3, 4, 5, 6, 7, 8, 9, 10, 11, 12, 13, 14, 15, 16, 17, 18, 19, 20, 21, 22, 23, 24, 25, 26, 27, 28, 29:
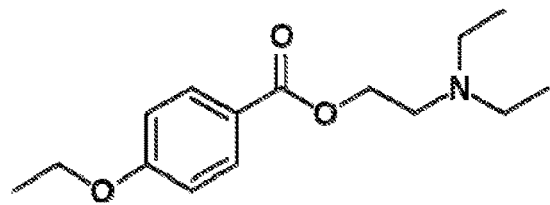
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30:
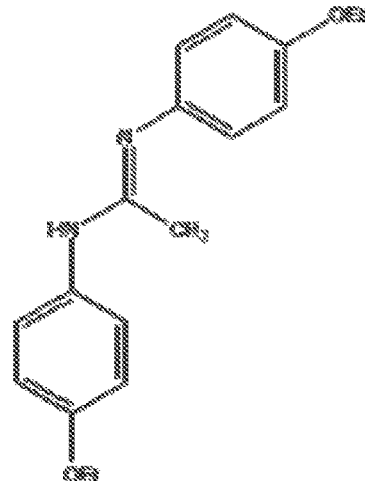
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31:
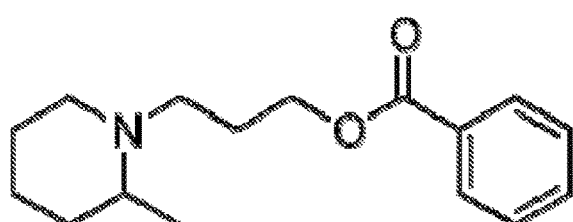
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
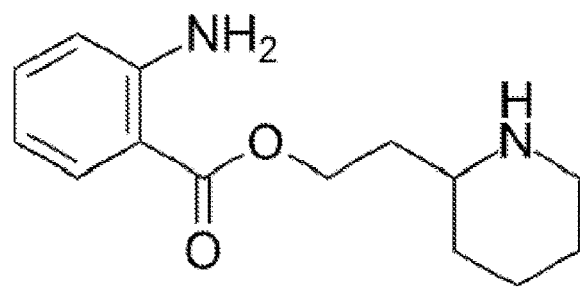
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
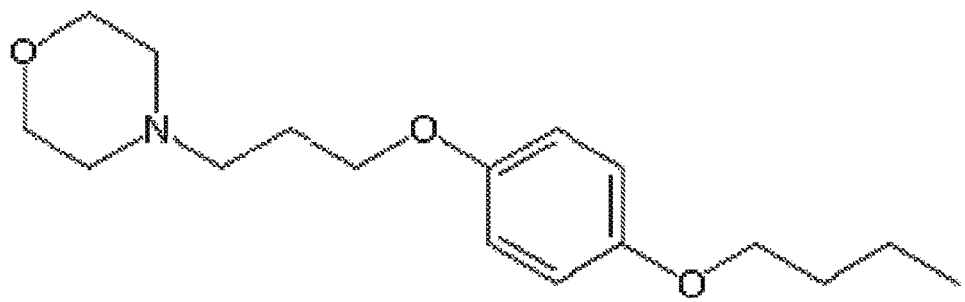
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
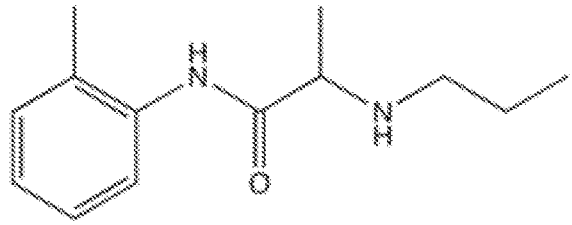
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
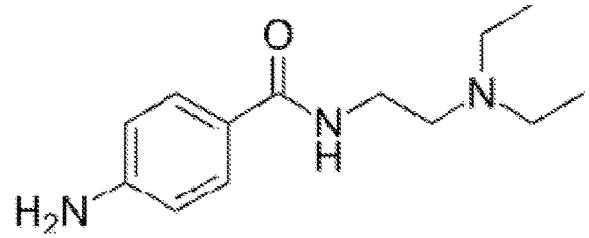
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
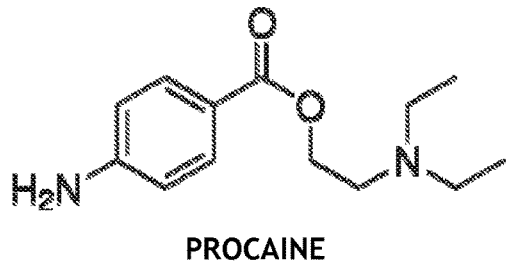
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
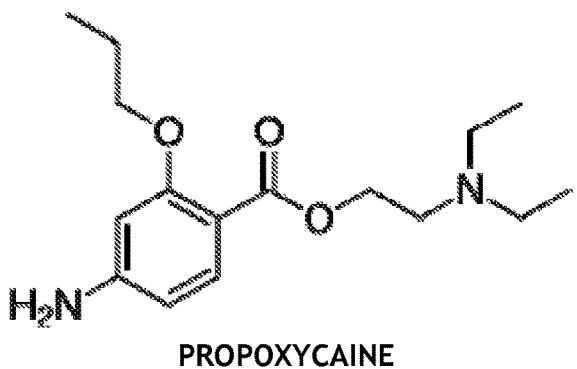
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
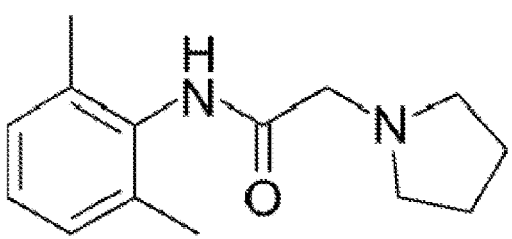
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
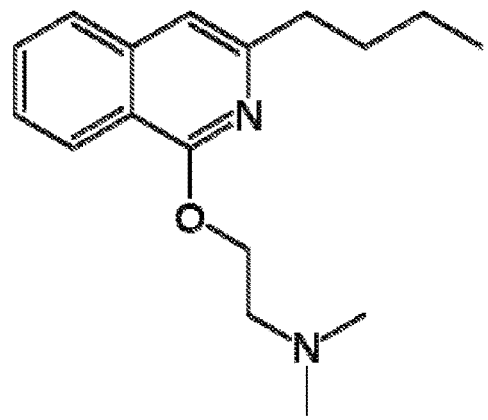
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
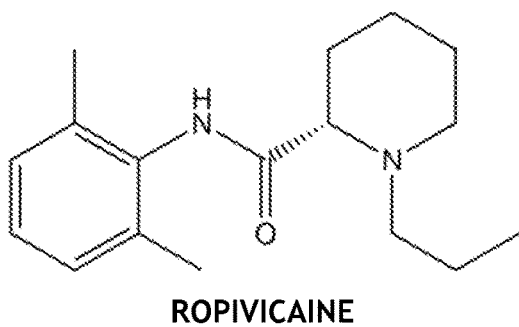
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
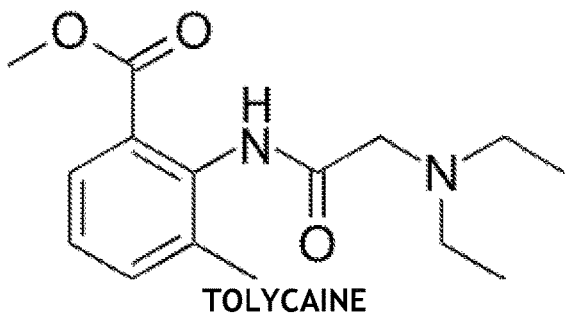
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
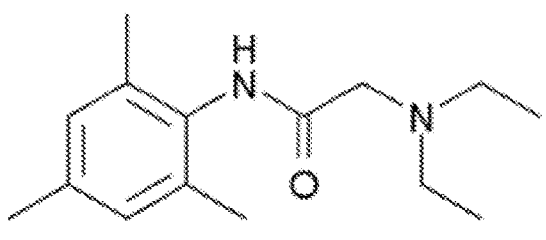
Figures 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
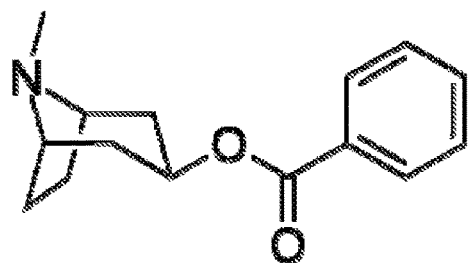
Figure 3:
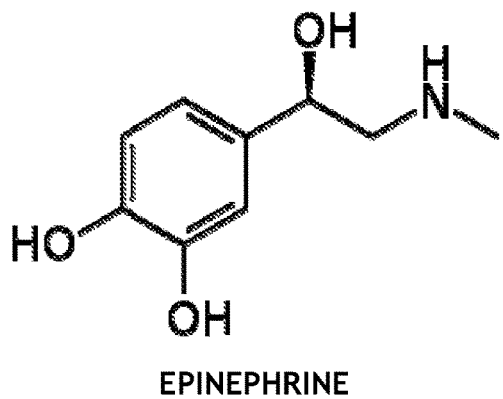
Figure 4:
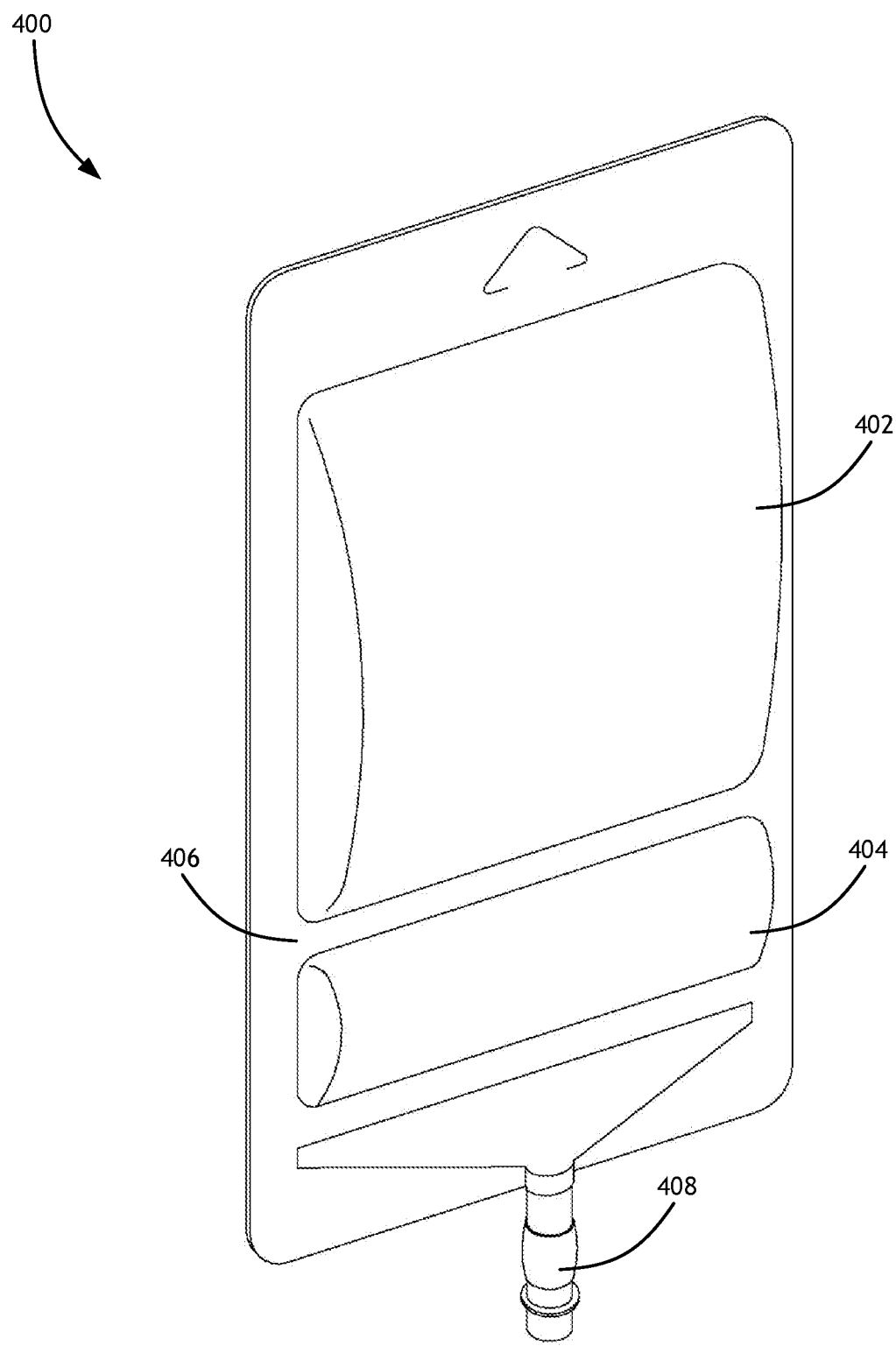
Figure 5:
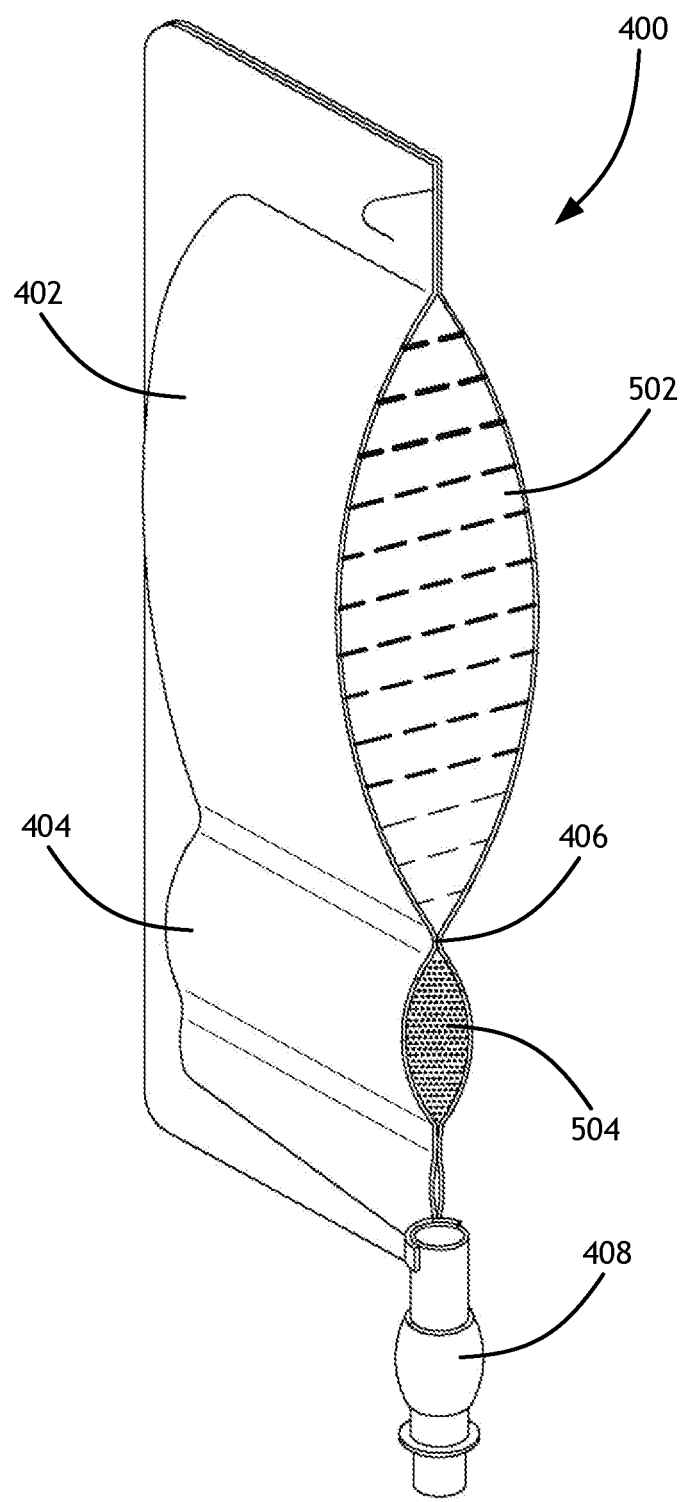
Figure 6:
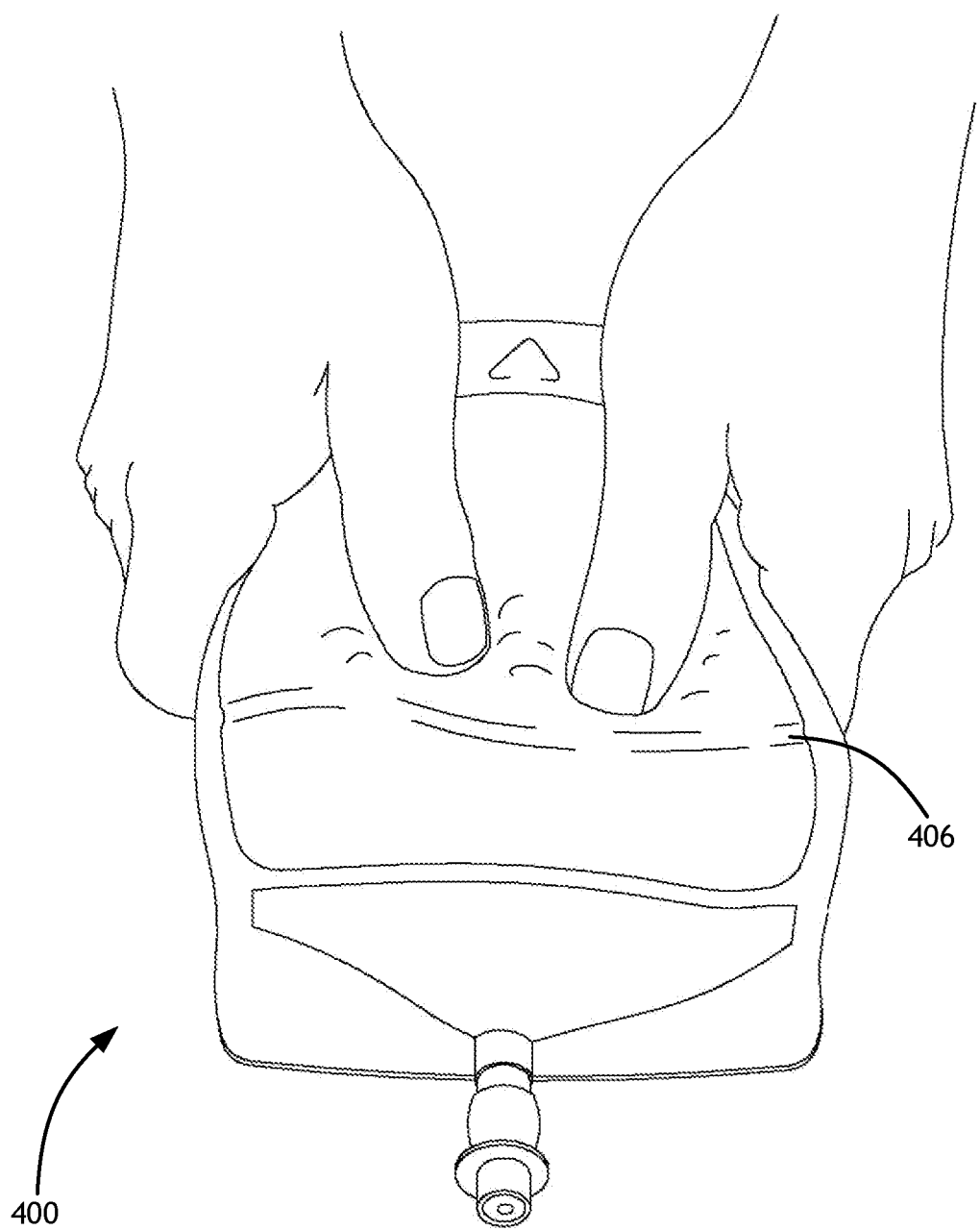
Figure 7:
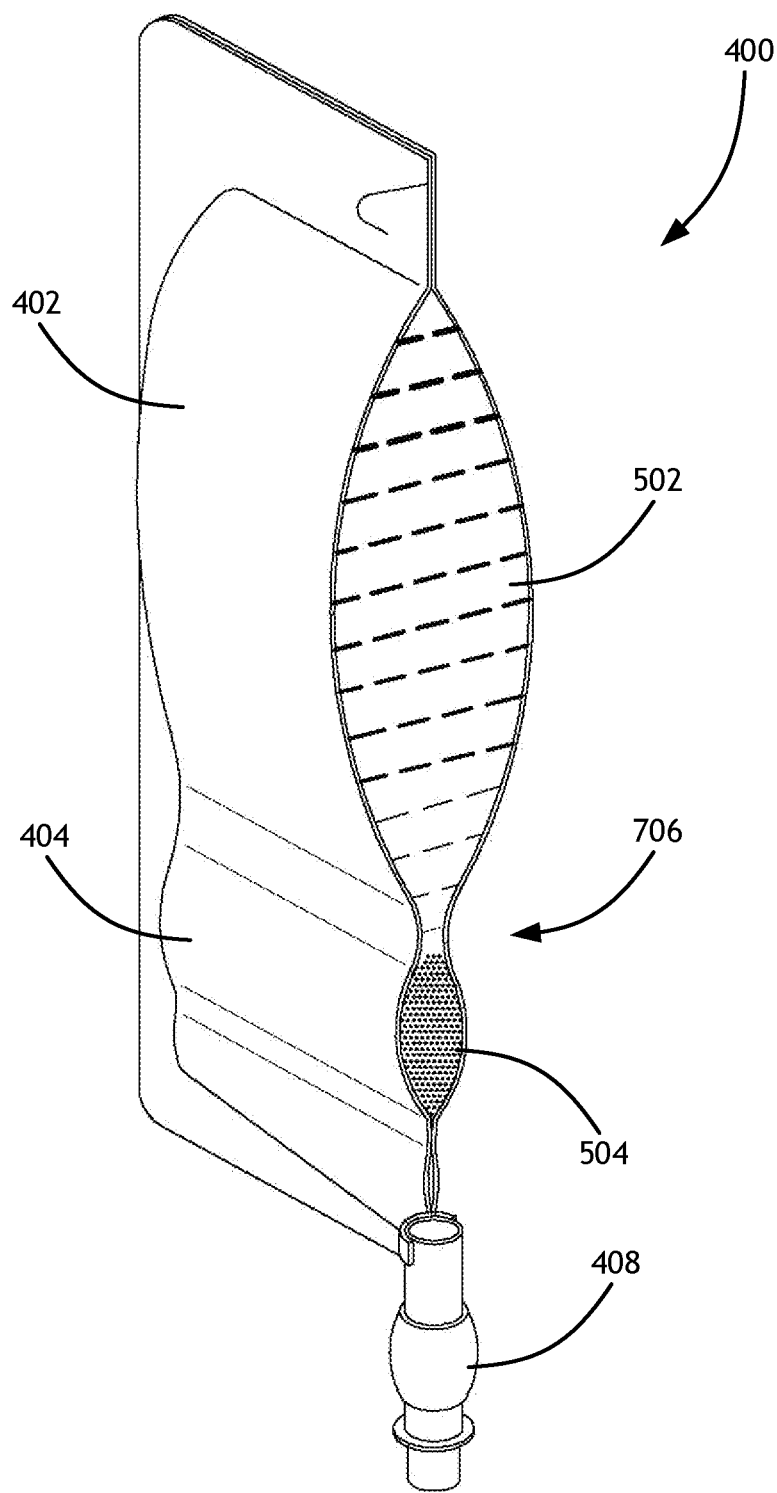
Figure 8:
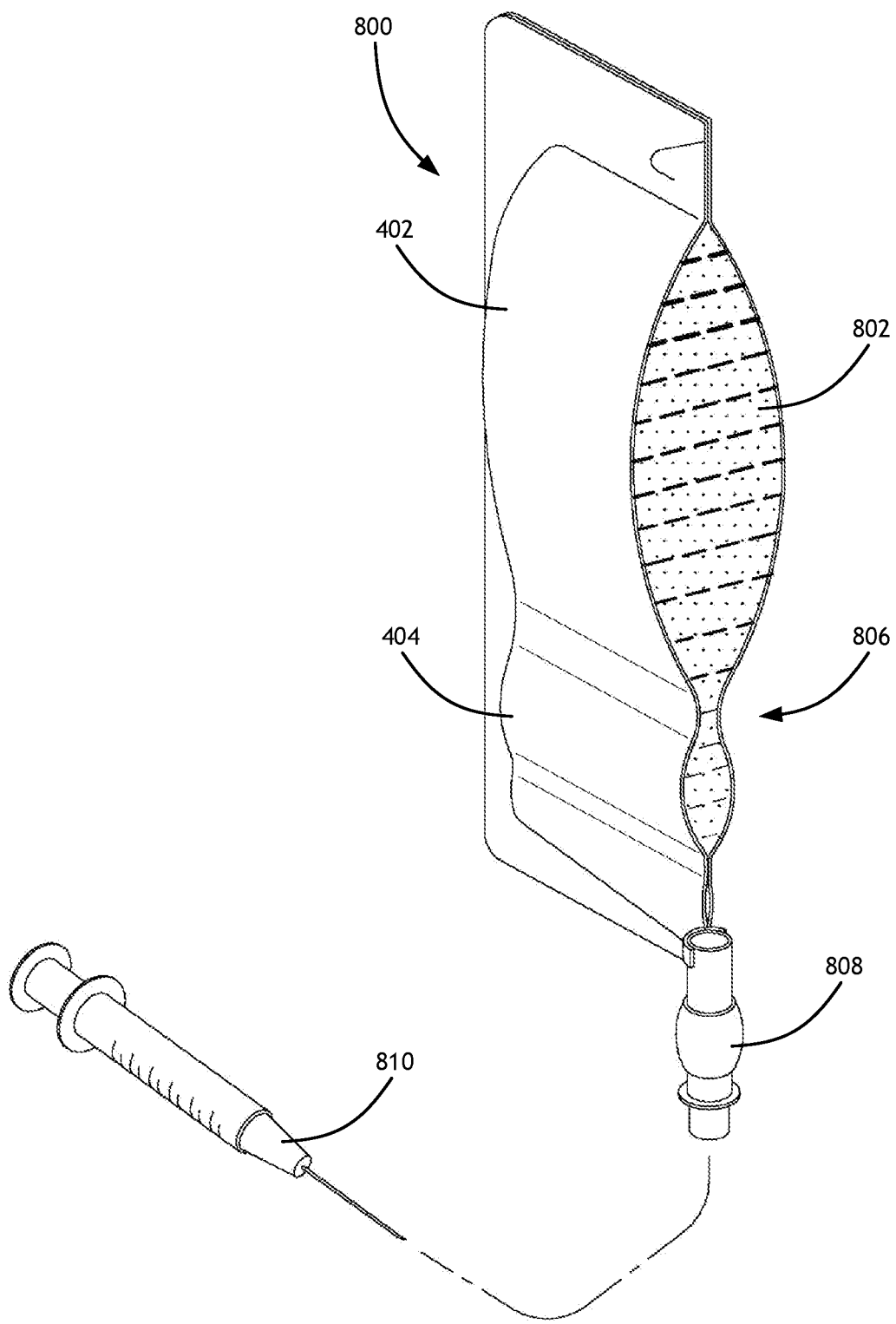
Figure 9:
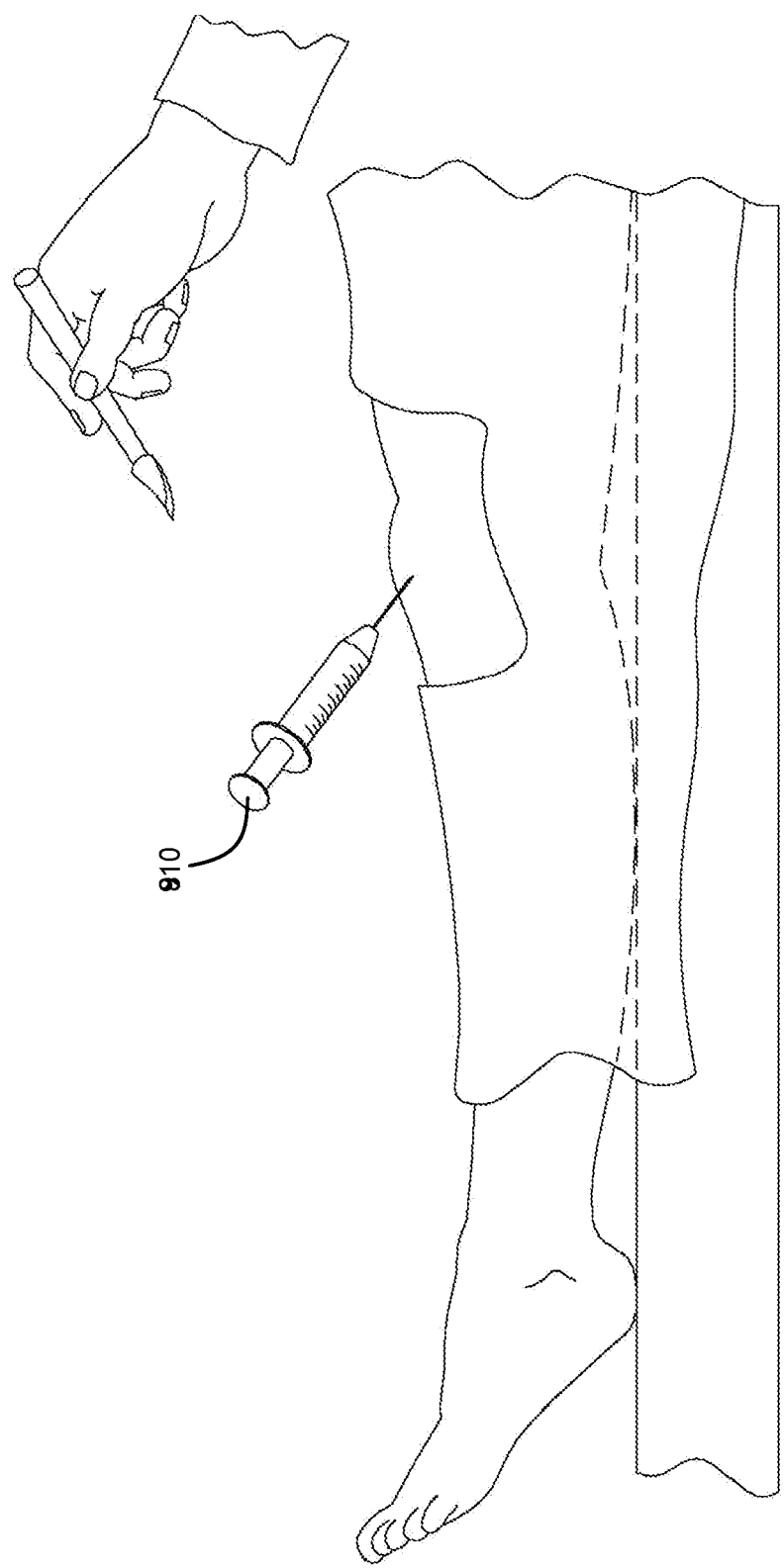

Referring to FIGS. 7 and 8, cross-sectional views of the package 400 shown in FIGS. 4 and 5 during mixing are shown. With application of sufficient pressure to the solution compartment 402, the breachable barrier is breached and a mixing channel 706 is formed between the solution compartment 402 and the powder compartment 404. Agitation of the solution compartment 402 facilitates mixing of the solution 502 and powdered tetracaine composition 504 into a mixed, extended duration local anesthetic solution 802. The extended duration local anesthetic solution 802 can be extracted via a syringe 810 and injected wherever local or regional anesthesia is desired.

In one embodiment, the solution compartment 402 contains approximately 30 cc to 100 cc of a 0.5% solution 502 of short duration local anesthetic and one part per 200,000 epinephrine while the powder compartment 404 contains approximately 60 mg to 240 mg of powdered tetracaine composition 504, resulting in a mixed, extended duration local anesthetic solution 802 comprising approximately 0.2% tetracaine. The safe range for tetracaine in solution is 0.15% to 0.55%; 0.2% is optimal to minimize motor block; 1% is toxic if applied directly to nerve structures. The extended duration local anesthetic solution 802 can be withdrawn using a sterile 30 cc-50 cc syringe 810 and a blunt needle or needleless withdrawal port, immediately upon mixing, and then injected into a desired location. Certain embodiments may include a sodium bicarbonate additive in the solution to render the mixed, extended duration local anesthetic less unpleasant upon injection.

A kit comprising a package 400 with premeasured quantities of short duration local anesthetic solution 502 and long duration powdered tetracaine composition 504 avoids unnecessary measuring and mixing at the point of care, saving time and minimizing the risk of medication error. Current technology would require mixing Tetracaine solution in multiple 2 cc glass ampules with a lidocaine solution, or some other short duration local anesthetic, at the time and site of use. Such mixing would occur outside the pharmacy, greatly raising the likelihood of medication error or contamination. Such process would also be labor intensive. A kit according to embodiments of the present invention would expedite the mixing process and ensure correct mixing, eliminating medication errors and contamination risk related to this process.

A kit according to embodiments of the present invention would provide extended shelf life and significant benefits to the military population in combat hospitals and in third world or military locations where refrigeration is not a viable option. A kit according to embodiments of the present invention would benefit such facilities in particular because many procedures that would otherwise not be performed for lack of a viable anesthetic option could be performed under local or regional anesthesia. Typically such locales have reduced capabilities to manage postoperative pain effectively. A kit according to embodiments of the present invention would benefit forward operating military facilities by allowing transportation of injured military personnel to a definitive facility, pain free from severe extremity trauma through the employment of regional anesthesia techniques with a long acting local anesthetic product.

Referring to FIG. 8, an environmental view of one embodiment according to the inventive concepts disclosed herein is shown. During a surgical procedure, an extended duration local anesthetic comprising a dilute short duration local anesthetic and tetracaine may be injected into a desired site via a syringe 810 to produce local analgesia, or regional analgesia through a nerve block.

Examples of regional anesthesia suitable for embodiments of the present invention include: interscalene blocks; infraclavicular blocks; supraclavicular blocks; axillary blocks; high wrist blocks; ulnar wrist blocks; radial nerve blocks; median nerve blocks; paraspinous/paravertebral nerve blocks; transversus abdominus plane blocks; lumbar plexus blocks; sciatic nerve blocks; femoral nerve blocks; adductor canal blocks; popliteal blocks; saphenous blocks; rectus sheath blocks; caudal epidural injections; T1-T4 paravertebral blocks; and intercostal blocks. Likewise, certain embodiments may be suitable for blind field blocks or in any application where local anesthesia is common such as digits, ears, penis, etc.

In at least one embodiment, a single-shot injection may be used in the epidural space. Epidural injections typically comprise 20-40 ml. The low motor blockade effect combined with the long duration of sensory block leads to prolonged analgesia with minimal mobility interference. While continuous infusion in the epidural space may be useful for some patients where prolonged duration of effect is secondary, maintaining a catheter in situ requires significantly more nursing care. Many facilities do not provide the type and number of experienced nurses necessary to closely monitor such catheters, so a long-acting, single shot product contributes to less intensive nursing care needs in patients.

Furthermore, embodiments of the present invention may be suitable for local or regional pain management apart from surgical procedures. Many pain management procedures would benefit from a long acting local anesthetic product with low toxicity and long duration. Such pain management procedures may include: C-2 ganglion blocks; occipital nerve blocks; trigger point injections; therapeutic medial branch blocks; all intra-articular joint injections; bursa injections; and enthesis/tendon injections. Pain management formulations may include a corticosteroid such as cortisone or other cortisone-type drug, or other drugs to further prolong the therapeutic effects of the embodiments.

Embodiments of the present invention are useful for longer acting local infiltration anesthesia. Provided areas infiltrated are not frankly bloody, the longer duration afforded by the tetracaine component will be present. Typically the maximum duration of effect is seen when a tissue plane or neurovascular sheath is available to serve as a reservoir.

Applications and quantities depend on the type of procedure. For surgical procedures, and in particular abdominal surgical procedures, 30 ml or more on each side of the abdomen may be used. TAP blocks are a recent development and are rapidly being adopted into the abdominal surgery arena as a reliable option for analgesia. The volume of anesthetic solution for TAP blocks range from 40 cc to 60 cc of local anesthetic solution. This involves a significantly higher total volume than most other types of blocks. Given this volume of solution, medication errors such as miscalculation of drug concentration or administration of wrong concentration are much more likely to result in toxicity and death using currently available medications. These types of errors are most likely to occur in the immediate perioperative period, where these medications are not reviewed for dose or concentration by a pharmacist. This embodiment would virtually eliminate the possibility of serious toxicity and death at the higher volumes of administration. Quantities of the extended duration local anesthetic described herein suitable for use in abdominal procedures would be generally safe. Similar quantities of existing mixtures would be toxic due to lipid preservatives necessary to maintain liposomal bupivacaine in solution and the inherent toxicity of bupivacaine, or necessary concentrations of other short duration local anesthetic in solution.

Embodiments of the present invention may be suitable for abdominal procedures such as: bowel surgery; hernia repair; appendectomy; cholecystectomy; hysterectomy; nephrectomy; cystectomy; and cesarean section. Embodiments of the present invention may be suitable for thoracic procedures such as: mastectomy; lung resection; and decortication. Embodiments of the present invention may be suitable for orthopedic procedures such as: fracture management; total knee/hip/shoulder replacement; amputations; ligament/joint reconstruction; and arthroscopy. Embodiments of the present invention may be suitable for spinal procedures such as: fusion; laminectomy; and discectomy. Embodiments of the present invention may be suitable for head and neck procedures such as: thyroidectomy; tonsillectomy/adenoidectomy; and septoplasty. Embodiments of the present invention may be suitable for plastic surgical procedures such as: liposuction; facial reconstruction; and breast reconstruction.

Because of the toxicity of high concentration alternatives, ultrasound for the performance of regional anesthetic techniques has grown significantly to identify the relevant neural structures for a given regional block so that a lesser total dose of high concentration local anesthetic may be used. The consequence of a smaller volume blocks is frequently a lesser duration of action. In many types of regional anesthesia, being able to use a larger volume of anesthetic in a tissue plane results in better quality anesthesia due to better contact with neural structures. This is particularly true for techniques that rely on blocking neural structures within an anatomic compartment of the body, such as the transversus abdominus plane, the adductor canal, the epidural space, or the neurovascular sheath. Being able to utilize larger volumes of local anesthetics in adequate concentrations to produce local anesthesia allows better pain relief overall. Additionally, the safety and the anticipated relatively low cost that the embodiments would provide, would allow patients potentially to undergo reapplication of blocks at 48-72 hours. This allows for analgesia throughout a protracted painful recovery such as occurs with certain abdominal surgical procedures, further reducing the need for narcotic analgesics.

Embodiments of the present invention have demonstrated peripheral and transversus abdominus plane blocks with analgesic effect for up to 36 hours or longer without adverse effects. Furthermore, the sensory blockade was generally prolonged to a much greater extent than the motor blockade, which is generally minimal.

Existing extended duration formulations are generally not safe for pediatric use. The embodiments described herein are directed toward concentrations of short duration local anesthetic and long duration local anesthetic with no contraindication for use in pediatric populations. Embodiments of the present invention would greatly benefit the pediatric population following high volume painful procedures such as tonsillectomy where the postoperative pain is difficult to control and leads to poor oral intake postoperatively.

Embodiments of the present invention may reduce or eliminate intraoperative and postoperative narcotics, which carry significant, deleterious side effects including nausea, vomiting, headaches, ileus, constipation, mental status changes, and potential issues of dependence and habituation.

When used therapeutically, the above-described compounds of the invention are administered in therapeutically effective amounts. In general, a therapeutically effective amount means that amount necessary to delay the onset of, inhibit the progression of, or halt altogether the particular condition being treated. Embodiments of the present invention may be applied to the treatment of chronic (e.g., neuropathic) pain as well as acute pain (e.g., inflammatory pain) that can occur following trauma, e.g., surgery, injury and so forth. Preferably, the condition being treated is a localized pain that is associated with, for example, postoperative analgesia, intractable cancer pain, chronic pain, shingles, phantom pain, rheumatoid arthritis, and painful diabetic neuropathy. As used herein, "local" refers to sensory processes signaling tissue injury (nociceptor).

A person skilled in the art will appreciate that therapeutic amounts will vary with patients age, condition, and sex, as well as the nature and extent of the disease, without undue experimentation. A therapeutically effective amount typically varies from 0.01 mg/kg to about 1000 mg/kg, preferably from about 0.1 mg/kg to about 200 mg/kg and most preferably from about 0.2 mg/kg to about 20 mg/kg, in one or more dose administrations daily, for one or more days. Where appropriate for local or regional use, adjustment to total dosage may be based primarily on patient habitus and secondarily on co-morbidities and type of surgery. Embodiments of the present invention described herein may be administered to a patient immediately before the patient is subjected or exposed to a pain-causing event (i.e., as pre-emptive analgesia), or while the patient is experiencing pain. Any conventional route, including injection, gradual infusion over time, infiltration anesthesia, regional anesthesia, or epidural anesthesia, or any other usual technique may be used. Pharmaceutically acceptable carriers include components that will not significantly impair the biological properties of the embodiments of the present invention, as understood by those skilled in the art.

Ten milliliters of at least one embodiment of the present invention contains 40 mg of lidocaine, 20 mg of tetracaine and 40 mcg of epinephrine. A typical application involves from 50 to 100 ml of solution, or a total of 200-400 mg of lidocaine, 100-200 mg of tetracaine, and 400 mcg of epinephrine. Total dose is adjusted to the specific purpose for the local anesthetic administration. Generally accepted toxic dose for lidocaine with epinephrine solution is 7 mg per kg total dose. In a 70 kg patient, that would be 490 mg of lidocaine; 90 mg more than the total provided by 100 ml of the present formulation. A range of toxic doses is found quoted in the literature for tetracaine, usually varying from 2.5 to 7.5 mg per kg. The middle of that range, 5 mg/kg is 350 mg in a 70 kg patient. Even at the lower range, 2.5 mg/kg is a total dose for the same patient of 175 mg. By comparison, 100 ml of the present formulation contains 200 mg of tetracaine. Given that the drug hydrolyzes immediately on contact with blood, an actual toxic dose is significantly higher than 5 mg/kg. The 7.5 mg/kg dose is 525 mg for a 70 kg patient. Clinical applications of embodiments of the present invention have not demonstrated any toxicity in a 70 kg patient with the 100 ml total dose.

Additional modalities may be employed for the administration of the agents. Both non-biodegradable and biodegradable polymeric matrices can be used to deliver the compositions described herein. Such polymers may be natural or synthetic polymers, and selected based on the period of time over which release is desired, generally in the order of a few hours to a year or longer. Typically, release over a period ranging from between a few hours and three to twelve months is most desirable. Other delayed onset formulations, including liposomal encapsulation may be employed.

Embodiments of the present invention relate to the treatment of pain and, in particular, to the alleviation of surgical pain and its varieties, e.g., neuropathic pain, and acute persistent pain by administration in various manners of a tetracaine and/or short duration local anesthetic mixture, with or without epinephrine or cortisone-type drugs.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages. The form herein before described being merely an explanatory embodiment thereof, it is the intention of the following claims to encompass and include such changes.

What is claimed is:

1. A method of using a solution for anesthesia in a patient, the method comprising:
  a. formulating a solution for injection into a patient, wherein the solution comprises lidocaine, epinephrine, and tetracaine;
  b. extracting the solution into a syringe; and
  c. injecting the solution into the patient to provide anesthesia to the patient.

2. The method of claim 1, wherein the anesthesia is local or regional.

3. The method of claim 2, wherein the anesthesia is regional and the solution is formulated for an injection selected from the group consisting of an interscalene block, an infraclavicular block, a supraclavicular block, an axillary block, a high wrist block, an ulnar wrist block, a radial nerve block, a median nerve block, a paraspinous/paravertebral nerve block, a transversus abdominus plane block, a lumbar plexus block, a sciatic nerve block, a femoral nerve block, an adductor canal block, a popliteal block, a saphenous block, a rectus sheath block, a caudal epidural injection, a T1-T4 paravertebral block, and an intercostal block.

4. The method of claim 2, wherein the anesthesia is local and the solution is formulated for a pain management injection selected from the group consisting of a C-2 ganglion block, an occipital nerve block, a trigger point injection, a therapeutic medial branch block, an intra-articular joint injection, a bursa injection, and an enthesis/tendon injection.

5. The method of claim 4, wherein the solution further comprises a corticosteroid.

6. The method of claim 5, wherein the corticosteroid is cortisone or a cortisone-type drug.

7. The method of claim 1, wherein the solution comprises between 0.25% and 5.0% by weight of lidocaine.

8. The method of claim 1, wherein the solution comprises between 0.15% and 0.55% by weight of tetracaine.

9. The method of claim 8, wherein the solution comprises 0.2% by weight of tetracaine.

10. The method of claim 1, wherein the solution comprises no more than one part per 50,000 of epinephrine.

11. The method of claim 1, wherein the solution comprises between one part per 250,000 and one part per 150,000 of epinephrine.

12. The method of claim 1, wherein the solution comprises one part per 200,000 of epinephrine.

13. The method of claim 1, wherein the solution further comprises sodium bicarbonate.

14. The method of claim 1, wherein the anesthesia is suitable for abdominal procedures, thoracic procedures, orthopedic procedures, spinal procedures, head and neck procedures, or plastic surgical procedures.

15. The method of claim 14, wherein the abdominal procedures are selected from the group consisting of bowel surgery, hernia repair, appendectomy, cholecystectomy, hysterectomy, nephrectomy, cystectomy, and cesarean section.

16. The method of claim 14, wherein the thoracic procedures are selected from the group consisting of mastectomy, lung resection, and decortication.

17. The method of claim 14, wherein the orthopedic procedures are selected from the group consisting of fracture management, total knee/hip/shoulder replacement, amputations, ligament/joint reconstruction, and arthroscopy.

18. The method of claim 14, wherein the spinal procedures are selected from the group consisting of spinal fusion, laminectomy, and discectomy.

19. The method of claim 14, wherein the head and neck procedures are selected from the group consisting of thyroidectomy, tonsillectomy/adenoidectomy, and septoplasty.

20. The method of claim 14, wherein the plastic surgical procedures are selected from the group consisting of liposuction, facial reconstruction, and breast reconstruction.

* * * * *